United States Patent
Edic et al.

(10) Patent No.: US 7,227,923 B2
(45) Date of Patent: Jun. 5, 2007

(54) METHOD AND SYSTEM FOR CT IMAGING USING A DISTRIBUTED X-RAY SOURCE AND INTERPOLATION BASED RECONSTRUCTION

(75) Inventors: Peter Michael Edic, Albany, NY (US); Samit Kumar Basu, Niskayuna, NY (US); Bruno Kristiaan Bernard De Man, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/108,419

(22) Filed: Apr. 18, 2005

(65) Prior Publication Data

US 2006/0233295 A1    Oct. 19, 2006

(51) Int. Cl.
A61B 6/00 (2006.01)
G01N 23/00 (2006.01)
H05G 1/70 (2006.01)
(52) U.S. Cl. ............... 378/9; 378/92; 378/115
(58) Field of Classification Search ........... 378/4, 378/5, 9, 15, 91, 92, 96, 98.6, 98.9, 114, 115, 378/119, 121, 134, 197, 95, 19, 901
See application file for complete search history.

(56) References Cited

U.S. PATENT DOCUMENTS

| | | | | | |
|---|---|---|---|---|---|
| 5,262,946 | A | * | 11/1993 | Heuscher | 378/15 |
| 5,305,363 | A | * | 4/1994 | Burke et al. | 378/4 |
| 5,335,255 | A | * | 8/1994 | Seppi et al. | 378/4 |
| 5,396,418 | A | * | 3/1995 | Heuscher | 378/15 |
| 5,438,605 | A | * | 8/1995 | Burke et al. | 378/135 |
| 5,832,051 | A | * | 11/1998 | Lutz | 378/8 |
| 5,966,422 | A | * | 10/1999 | Dafni et al. | 378/9 |
| 6,353,653 | B1 | * | 3/2002 | Edic | 378/8 |
| 6,370,217 | B1 | * | 4/2002 | Hu et al. | 378/8 |
| 6,421,412 | B1 | * | 7/2002 | Hsieh et al. | 378/9 |
| 6,819,738 | B2 | * | 11/2004 | Hoffman | 378/19 |
| 6,879,656 | B2 | * | 4/2005 | Cesmeli et al. | 378/4 |
| 6,909,769 | B2 | * | 6/2005 | Bruder et al. | 378/8 |
| 6,937,689 | B2 | * | 8/2005 | Zhao et al. | 378/9 |
| 2002/0131544 | A1 | * | 9/2002 | Aradate et al. | 378/4 |
| 2003/0007593 | A1 | * | 1/2003 | Heuscher et al. | 378/4 |
| 2003/0123718 | A1 | | 7/2003 | Edic et al. | |

(Continued)

OTHER PUBLICATIONS

Peter Michael Edic et al., "Method and Apparatus for Generating Temporally Interpolated Projections", U.S. Appl. No. 10/625,321, filed Jul. 23, 2003, GE Reference.

(Continued)

Primary Examiner—Edward J. Glick
Assistant Examiner—Anastasia S. Midkiff
(74) Attorney, Agent, or Firm—Jean K. Testa; Curtis B. Brueske

(57) ABSTRACT

A method for Computed Tomography (CT) imaging is provided. The method comprises rotating a gantry at a substantially slow rotation speed about a volume of interest. The gantry comprises a combination of X-ray source points. The X-ray source points comprise one or more discrete emission points and an arc of discrete or continuous X-ray source points. The method then comprises obtaining projection data from the combination of X-ray source points and performing a suitable reconstruction based on the projection data obtained from the combination of X-ray source points, to generate one or more reconstructed images.

21 Claims, 4 Drawing Sheets

U.S. PATENT DOCUMENTS

2004/0136490 A1* 7/2004 Edic et al. .................... 378/4
2004/0218719 A1* 11/2004 Brown et al. ................. 378/95
2005/0058248 A1* 3/2005 Klingenbeck-Regn ....... 378/95
2005/0100126 A1* 5/2005 Mistretta et al. ............. 378/15
2005/0147199 A1* 7/2005 Dunham et al. ............... 378/5
2005/0185758 A1* 8/2005 Bruder et al. ................. 378/65

OTHER PUBLICATIONS

Bruno De Man et al., "Method and System for Imaging Using Multiple Offset X-Ray Emission Points", U.S. Appl. No. 10/789,539, filed Feb. 27, 2004, GE Reference.

* cited by examiner

METHOD AND SYSTEM FOR CT IMAGING USING A DISTRIBUTED X-RAY SOURCE AND INTERPOLATION BASED RECONSTRUCTION

BACKGROUND

The invention relates generally to the field of CT imaging and more specifically to a distributed source configuration for the imaging of dynamic internal tissues. In particular, the invention relates to an interpolation-based reconstruction technique for performing full field of view imaging of dynamic internal tissues, using the source configurations.

Computed tomography (CT) imaging systems measure the attenuation of X-ray beams passed through a patient from numerous angular positions about the patient. Based upon these measurements, a computer is able to reconstruct images of the linear attenuation coefficient of the portions of a patient's body responsible for the radiation attenuation. As will be appreciated by those skilled in the art, these images are based upon separate examination of a series of angularly displaced images of the transmitted X-ray beam intensity. A CT system processes X-ray intensity data to generate two-dimensional (2D) maps of the line integral of linear attenuation coefficients of the scanned object at multiple view angle positions about the object, denoted as projection data. These data are then reconstructed to produce one or more images, which are typically displayed on a monitor, and may be printed or reproduced on film. A virtual three-dimensional (3D) image may also be produced by a CT examination.

CT scanners operate by projecting fan-shaped or cone-shaped X-ray beams from an X-ray source. The X-ray beams may be collimated to control the shape and spread of the beams. The X-ray beams are attenuated as they pass through the object to be imaged, such as a patient. The attenuated beams are detected by a set of detector elements. Each detector element produces a signal affected by the attenuation of the X-ray beams, and the data are processed to produce signals that represent the line integrals of the attenuation coefficients of the object along the X-ray paths. These signals are typically called "projection data" or just "projections". By using known reconstruction techniques, such as filtered backprojection, useful images may be formulated from the projection data. The images may in turn be associated to form a volume rendering of a region of interest. In a medical context, pathologies or other structures of interest may then be located or identified from the reconstructed images or a rendered volume.

CT imaging techniques, however, may present certain challenges when imaging dynamic internal tissues, such as the heart. For example, in cardiac imaging, the motion of the heart causes inconsistencies in the projection data, which, after reconstruction, may result in various motion-related image artifacts such as blurring, streaking, or discontinuities. To reduce the occurrence of motion-related image artifacts, various techniques may be employed to improve the temporal resolution of the imaging system, thereby reducing the effects of the moving tissue. Temporal resolution may generally be improved by decreasing the rotation time of the CT gantry. In this way, the amount of motion that occurs within the temporal window associated with the acquisition of a projection data set is minimized.

Temporal resolution may be further improved by the choice of reconstruction algorithm. For example, segment reconstruction algorithms, such as half-scan reconstruction algorithms, may be employed in the reconstruction process. The segment reconstruction algorithms typically reconstruct images using projection data collected over an angular range of 180° plus the fan angle ($\beta$) of the X-ray beam. Because the acquisition of projection data during gantry rotation of 180°+$\beta$ requires less time when compared to acquisition occurring during 360° of gantry rotation, the temporal resolution in the reconstructed images is improved.

Multi-sector reconstruction techniques may also improve the temporal resolution of the reconstructed images by using projection data acquired during multiple rotations of the gantry by a multi-slice detector array. The projection data set used for reconstruction are composed of two or more sectors of projection data that are acquired during different cardiac cycles. The sectors comprise the data acquired during a short span of the gantry rotation, typically less than half of a rotation. The sectors, therefore, have good temporal resolution if acquired by a rapidly rotating gantry, thereby providing good effective temporal resolution for the aggregate projection data set used in reconstruction.

Using the techniques discussed above, third and fourth generation CT systems are capable of temporal resolutions of approximately 250 ms using segment reconstruction techniques. Fifth generation CT systems, utilizing a stationary detector ring and an electron gun which sweeps an electron beam along a stationary target ring to generate x-rays, are capable of achieving a temporal resolution of approximately 50 ms or less. A temporal resolution of approximately 20 ms, however, is desirable in order to "freeze" cardiac motion, thereby minimizing motion-related artifacts in the reconstructed images. While such fifth generation systems could be made to scan faster, they suffer from a non co-planar detector and source configuration. The fact that the source and detector do not rotate means that at some subset of angles in the scan, the detector is occluded by the source (or visa versa). As a result, such systems tend to collect incomplete data, and suffer from image artifacts as a result. For third generation CT systems, improving temporal resolution in addition to the above techniques has typically focused on further increasing the rotational speed of the gantry.

However, as the rotational speed of the gantry increases, the centripetal force required for gantry components also increases. The increasing centripetal force and the tolerances of the gantry components may comprise, therefore, a mechanical limitation to increases in gantry angular velocity. Furthermore, to obtain consistent image quality in terms of signal-to-noise ratio, a high integrated X-ray flux should be delivered to the imaged object or patient during the scan interval. However, achieving a high integrated X-ray flux for faster rotation of the gantry requires increased instantaneous X-ray flux and places increased demand on the X-ray tube, particularly in regard to tube output, and on the components that cool the X-ray tube. Both mechanical and X-ray flux considerations, therefore, are obstacles to increasing the gantry rotation speed sufficiently to achieve a temporal resolution of 20 ms or better in CT reconstructions. A technique for achieving a high temporal resolution without increasing gantry rotation speed is therefore desirable.

Furthermore, it is also desirable to develop CT scanners with high spatial and temporal resolution, good image quality, and good coverage along the z-axis, i.e., the longitudinal axis of the CT scanner. However, existing systems typically acquire projection data for a limited extent of the patient or object being scanned. Therefore, it may be desirable to increase the coverage of the detector in one or more dimensions to facilitate measurement of projection data from the entire portion of the object or subject being scanned. For example, longitudinal axis coverage of the detector may be improved by increasing the number of rows of detector elements in the detector. This approach has lead to the development of CT systems with larger detectors. Larger detectors, however, may be undesirable for a variety of reasons. For instance, as one might expect, larger detectors and associated acquisition electronics are both more costly and more difficult to produce. In addition, the mechanical subsystem responsible for supporting and/or rotating a larger detector may also need to be larger and more complex and/or may be subject to greater mechanical stress. Furthermore, large detectors are associated with increased cone angles, i.e., the angle between the source and the detector periphery in the longitudinal direction. The increased cone angle between the source and detector periphery is in turn associated with increased cone-beam artifacts in the reconstructed images depending on the choice of data acquisition protocol and reconstruction algorithm. When the cone angle increases beyond a certain limit, the degradation of the image quality may become severe for axial, or step-and-shoot scanning. For the foregoing reasons, increasing the scan coverage by simply increasing the detector coverage, i.e., size of the detector, is not a sufficient or complete solution.

A technique for achieving high spatial resolution and high temporal resolution, good image quality, and good coverage using a standard or smaller detector is therefore desirable. In addition, it is also desirable to develop a technique for achieving high temporal resolution without substantially increasing the rotation speed of the gantry.

BRIEF DESCRIPTION

Embodiments of the present invention address these and other needs. In one embodiment, a method for Computed Tomography (CT) imaging is provided. The method comprises rotating a gantry at a substantially slow rotation speed about a volume of interest. The gantry comprises a combination of X-ray source points. The X-ray source points comprise one or more discrete emission points and an arc of discrete or continuous X-ray source points. The method then comprises obtaining projection data from the combination of X-ray source points and performing a suitable reconstruction based on the projection data obtained from the combination of X-ray source points, to generate one or more reconstructed images.

In another embodiment, a method for Computed Tomography (CT) imaging is provided. The method comprises rotating a gantry at a substantially slow rotation speed about a volume of interest. The gantry comprises one or more discrete emission points and an arc of discrete or continuous X-ray source points. The method further comprises obtaining a first projection data set and a second projection data set. The first projection data set comprises a plurality of projections, and is obtained by individually activating the one or more discrete emission points at multiple angular positions about the volume of interest. The second projection data set comprises obtaining a plurality of projections at a plurality of view angle positions, and is obtained by activating the arc of discrete or continuous X-ray source points to emanate X-ray beams illuminating a central region of interest. Then, the method comprises interpolating the plurality of projections comprising the second projection data set to generate a set of time-resolved, interpolated projections. Each interpolated projection characterizes the projection data from the central region of interest at a particular instant in time. Finally, the method comprises combining the first projection data set and the set of interpolated projections to generate one or more time-resolved reconstructed images.

In yet another embodiment, a Computed Tomography (CT) imaging system is provided. The system comprises a gantry configured to rotate at a substantially slow rotation speed about a volume of interest. The gantry comprises one or more discrete emission points and an arc of discrete or continuous X-ray source points. The one or more discrete emission points are configured to individually emit streams of radiation at multiple angular positions about the volume of interest and the arc of discrete or continuous X-ray source points is configured to emanate X-ray beams illuminating a central region of interest. The system further comprises a detector and a computer. The detector is configured to detect the streams of radiation from the one or more discrete emission points and the arc of discrete or continuous X-ray source points, and generate one or more signals responsive to the streams of radiation. The computer is configured to receive and process the one or more signals from the detector to generate projection data and perform a suitable reconstruction on the projection data, to generate one or more reconstructed images.

DRAWINGS

These and other features, aspects, and advantages of the present invention will become better understood when the following detailed description is read with reference to the accompanying drawings in which like characters represent like parts throughout the drawings, wherein.

Figure 4:
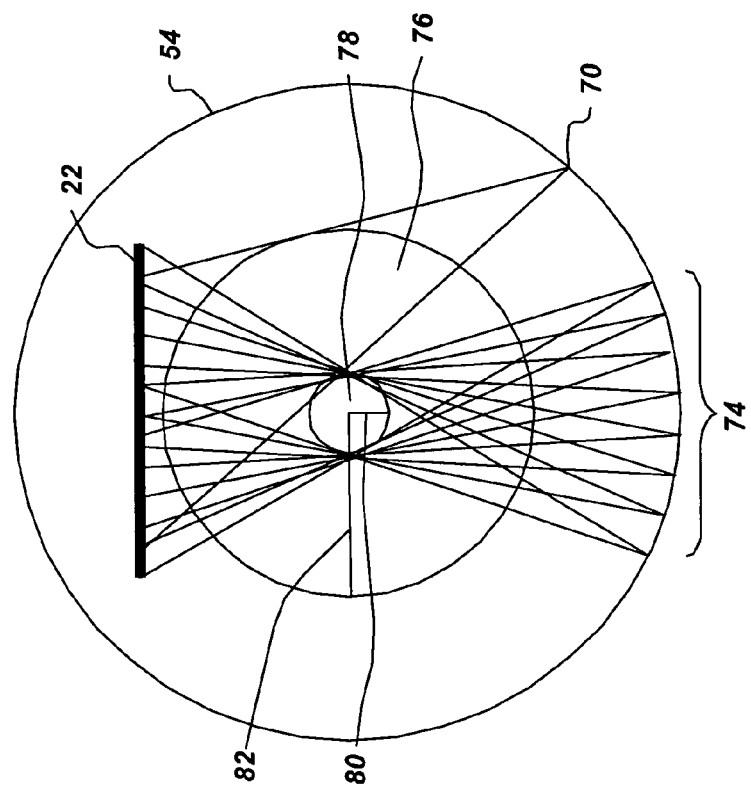
Figure 5:
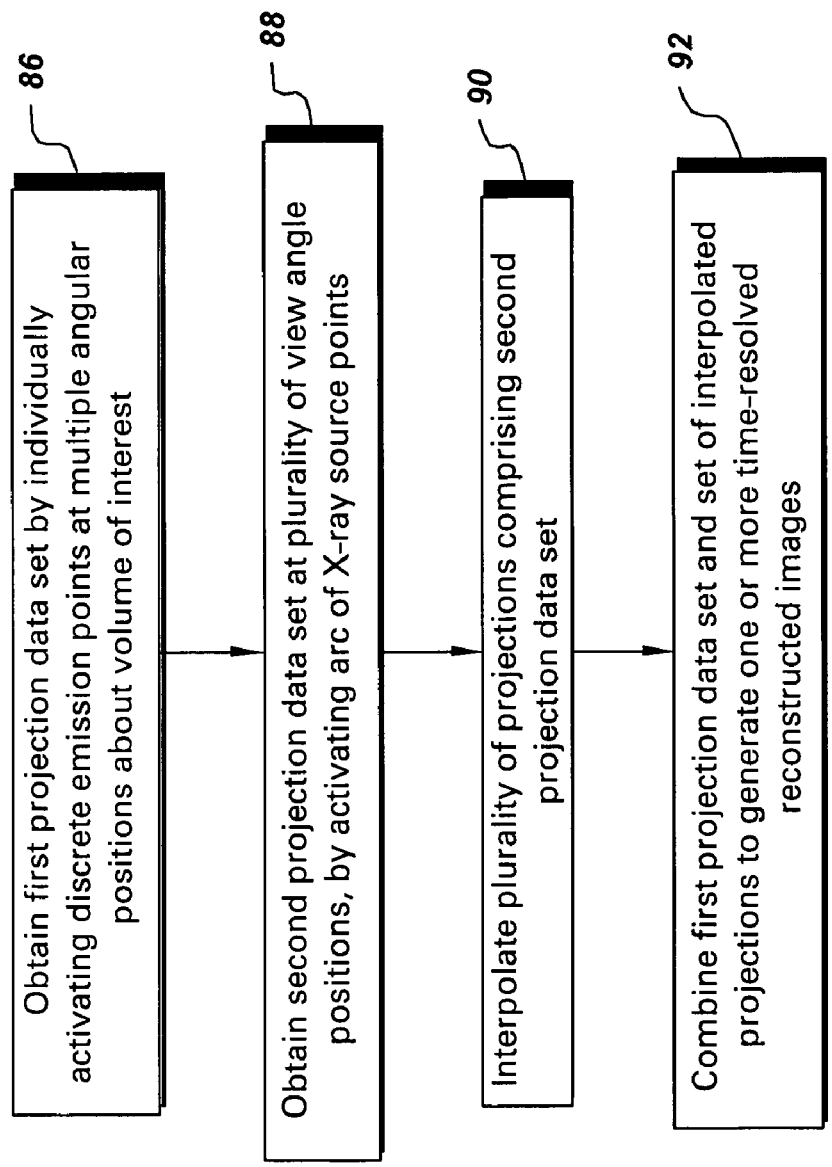

FIG. 4 is a diagrammatical illustration of a distributed source configuration for acquiring projection data in accordance with another aspect of the present technique; and FIG. 5 is a flowchart showing exemplary logic, including exemplary steps for generating projection data and processing the projection data to generate one or more reconstructed images, in accordance with one aspect of the present technique.

DETAILED DESCRIPTION

Figure 1:
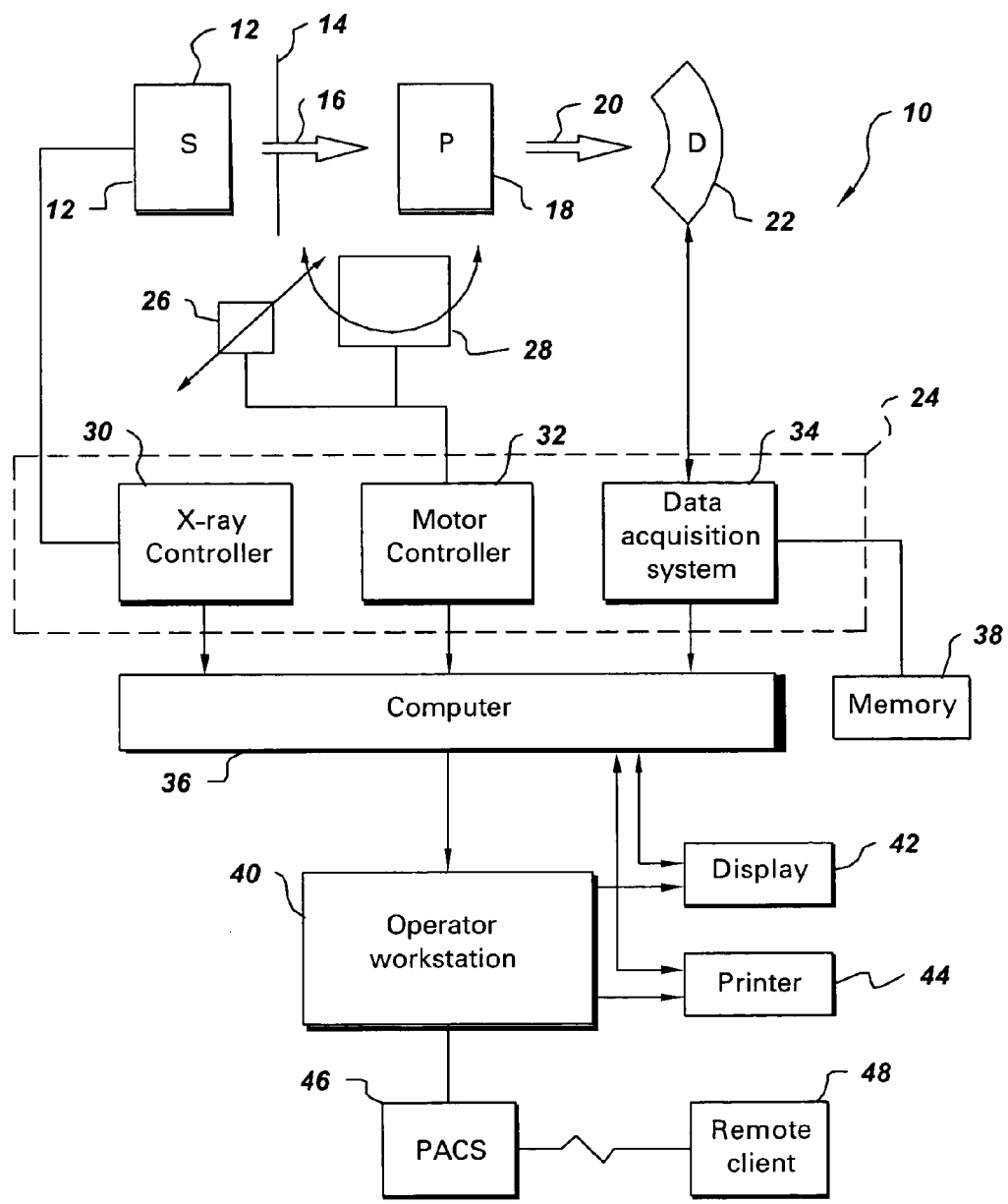
FIG. 1 illustrates diagrammatically an imaging system 10 for acquiring and processing image data, in accordance with one aspect of the present technique.

FIG. 1 illustrates diagrammatically an imaging system 10 for acquiring and processing image data, in accordance with one aspect of the present technique. In the illustrated embodiment, system 10 is a computed tomography (CT) system designed to acquire X-ray projection data, to reconstruct the projection data into an image and to process the image data for display and analysis in accordance with the present technique. Though the imaging system 10 is discussed in the context of medical imaging, the techniques and configurations discussed herein are applicable in other non-invasive CT imaging contexts, such as baggage or package screening.

In the embodiment illustrated in FIG. 1, the CT imaging system 10 includes a distributed source 12 of X-ray radiation positioned adjacent to a collimator 14. As described herein, the CT imaging system 10 may be configured in a variety of ways to improve spatial and temporal resolution, to improve image quality, and/or to improve longitudinal coverage. Also, as described herein, various source 12 and detector 22 configurations are implemented which improve one or more of these parameters. In accordance with one aspect of the present technique, the distributed source 12 of X-ray radiation includes one or more discrete, i.e., separated, emission points. For example, a conventional X-ray tube may be equated with a single emission point. Alternatively, an X-ray source such as any solid-state X-ray source having electron emitters using field emission, or an X-ray source utilizing thermionic electron emitters may include multiple emission points. Examples of suitable electron emitters include tungsten filament, tungsten plate, field emitter, thermal field emitter, dispenser cathode, thermionic cathode, photo-emitter, and ferroelectric cathode. Such solid-state or thermionic X-ray sources may be configured such that the respective emission points form an arc or a stationary ring. Also, as discussed herein, and in accordance with another aspect of the present technique, the source 12 of X-ray radiation also includes an arc of X-ray source points that includes one or more addressable X-ray focal spots. It should also be noted that the one or more discrete X-ray sources and the arc of discrete or continuous X-ray source points that are mentioned throughout the present patent application can either be configured to lie in a single plane or be distributed along the longitudinal axis of the scanner. In this manner, cone-beam artifacts in reconstructed images can be reduced or eliminated.

Though the present description may discuss the rotation of an X-ray source 12, as may occur in conventional third-generation CT systems, one of ordinary skill in the art will appreciate that discussion of rotating an X-ray source 12 also encompasses functional equivalents. For example, for a solid-state X-ray source 12 configured as a ring, the emission points that comprise the X-ray source 12 may not mechanically rotate about a field of view. Instead, the emission points that are disposed in the ring may be activated in a sequential manner effectively equivalent to rotating an X-ray source 12. Therefore, where an X-ray source 12 or emission point is described as rotating, it is to be understood that such a rotation may result from the physical rotation of the source 12 or elements of source 12 or from such a functional equivalent. Moreover, a single ring containing multiple X-ray emission points may comprise the one or more discrete X-ray sources and the arc of discrete or continuous X-ray source points.

Referring to FIG. 1, collimator 14 permits a stream of radiation 16 to pass into a region in which an object, such as a human patient, 18 is positioned. The stream of radiation may be generally cone-shaped, depending on the configuration of the detector array, as well as the desired method of data acquisition. A portion of the radiation 20 passes through or around the object and impacts a detector array, represented generally at reference numeral 22. Detector elements of the array produce electrical signals that represent the intensity of the incident X-ray beam. These signals are acquired and processed to reconstruct an image of the features within the object. Detector 22 may be a linear detector array or a two-dimensional area detector.

Source 12 is controlled by a system controller 24, which furnishes power, focal spot location, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the object 18. It should be noted that the rotational subsystem 28 might include a gantry. Thus, the system controller 24 may be utilized to operate the gantry. The linear positioning subsystem 26 enables the patient 18, or more specifically a table, to be displaced linearly. Thus, the table may be linearly moved within the gantry to generate images of particular areas of the patient 18. Alternatively, in the screening of packages or luggage for security and inspection applications, the linear positioning subsystem may be a conveyer belt.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled digital or analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote client 48, such as a radiology department information system (RIS), hospital information system (HIS) or to an internal or external network, so that others at different locations may gain access to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The system controller 24 comprising the X-ray controller 30, the motor controller 32, and the data acquisition system 34 may be one device or the individual controllers contained therein may be separate devices.

Figure 2:
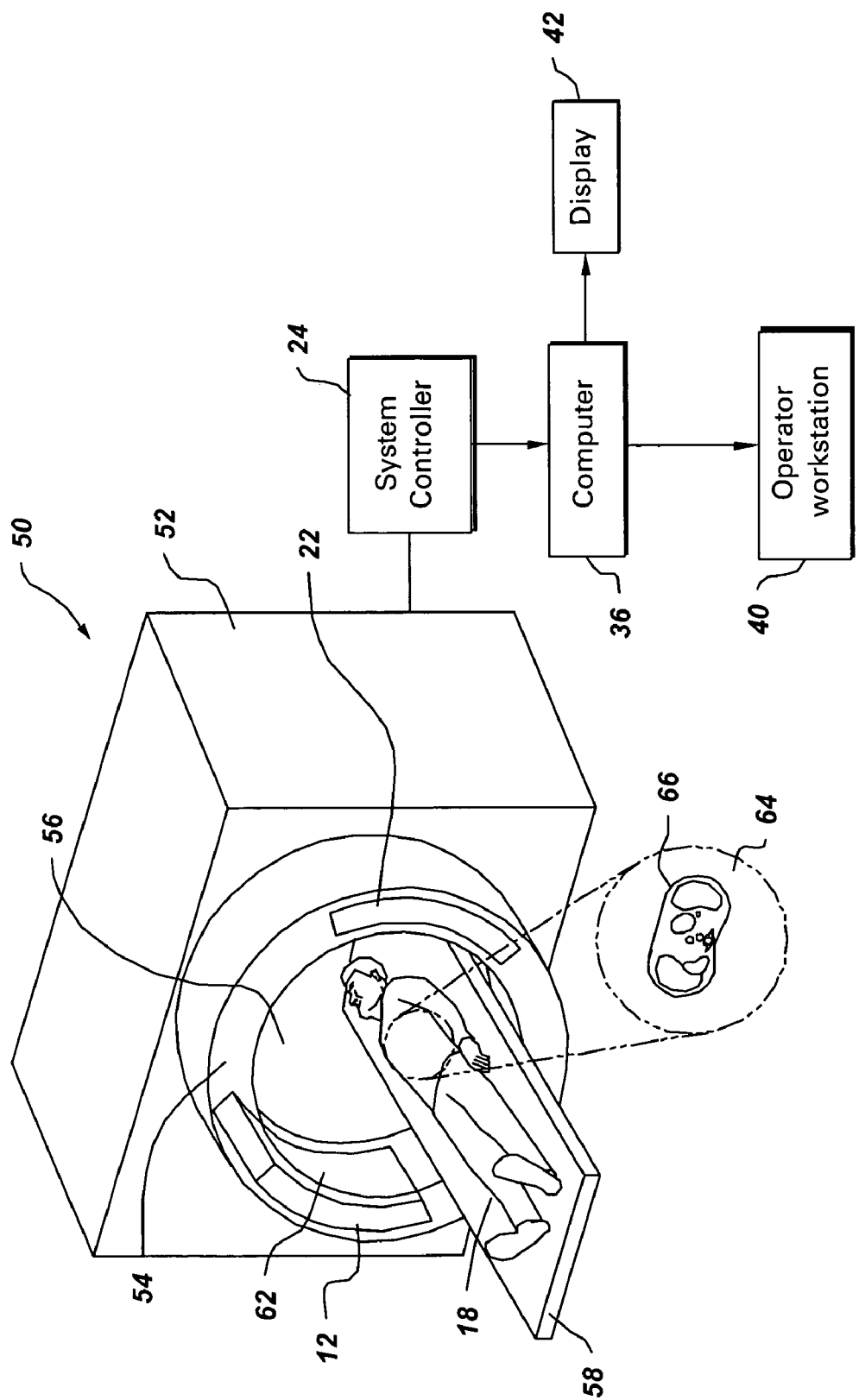
FIG. 2 is a diagrammatical view of a physical implementation of the CT system of FIG. 1, in accordance with one aspect of the present technique.

Referring generally to FIG. 2, an exemplary imaging system utilized in a present embodiment may be a CT scanning system 50. The CT scanning system 50 may be a volumetric CT (VCT) system utilizing cone-beam geometry and an area detector to allow the imaging of a volume of interest, such as a chest region of the patient 18. Furthermore, as noted above, the CT scanning system 50 may be a modified third generation CT imaging system, as depicted, or may be a later generation CT imaging system.

The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, such as via linear displacement of the table 58 by the linear positioning subsystem 26 (see FIG. 1). In accordance with a particular aspect of the present technique, and as will be described in greater detail below, the gantry 54 includes one or more discrete emission points and an arc of discrete or continuous X-ray source points. Activation of the emission points may be coordinated so that only one is active at a time, such as by employing an alternating activation scheme. In this manner, each emission point, when active, may provide a subset of the projection data required to reconstruct an object within a given field of view. Combination of these subsets, however, allows the reconstruction of the entire field of view. In addition, because only a subset of the projection data associated with the field of view are acquired at one time, the in-plane extent of the detector 22 may be reduced. Indeed, the in-plane extent of the detector 22 may be reduced to the degree that a flat-panel detector may be employed. The arc of discrete or continuous X-ray source points typically includes one or more X-ray sources that emit X-ray radiation from one or more focal points 62.

In accordance with the present technique, the one or more discrete emission points and the arc of discrete or continuous X-ray source points along the gantry 54 are activated to project beams of X-rays toward the detector array 22. Further, in accordance with an exemplary operation of the present technique, and as will be described in greater detail below, the one or more discrete emission points are configured to individually emit streams of radiation at multiple angular positions about a volume of interest and the arc of discrete or continuous X-ray source points are configured to emanate X-ray beams illuminating a central region of interest.

The collimator 14 (see FIG. 1), such as lead or tungsten shutters, typically defines the size and shape of the projected X-rays that emerge from the X-ray source 12. The detector 22, such as an area detector in the case of a VCT system, is generally formed by a plurality of detector elements, which detect the X-rays that pass through and around a subject of interest, such as the heart or chest. Each detector element produces an electrical signal that represents the intensity of the X-ray beam at the position of the element during the time interval when the beam strikes the detector. The gantry 54 is rotated around the subject of interest so that a plurality of radiographic views may be collected by the computer 36.

Thus, as the gantry 54 and the detector 22 rotate, the detector 22 collects data corresponding to the attenuated X-ray beams. Data collected from the detector 22 then undergoes pre-processing and calibration to condition the data to represent the line integrals of the attenuation coefficients of the scanned objects. The processed data, commonly called projections, may then be filtered and back-projected to formulate an image of the scanned area. A formulated image may incorporate, in certain modes, projection data acquired for an angular rotation of the gantry of less or more than 360 degrees.

In one embodiment, once reconstructed, the image produced by the system of FIGS. 1 and 2 reveals the chest and heart region of the patient 18. As illustrated generally in FIG. 2, the image 64 may be displayed to show patient features, such as indicated at reference numeral 66 in FIG. 2. In traditional approaches to diagnosis of medical conditions, such as disease states, and more generally of medical conditions or events, a radiologist or physician would consider the reconstructed image 64 to discern characteristic features of interest. Such features 66 include coronary arteries or stenotic lesions of interest, and other features, which would be discernable in the image, based upon the skill and knowledge of the individual practitioner. Other analyses may be based upon capabilities of various CAD algorithms.

Figure 3:
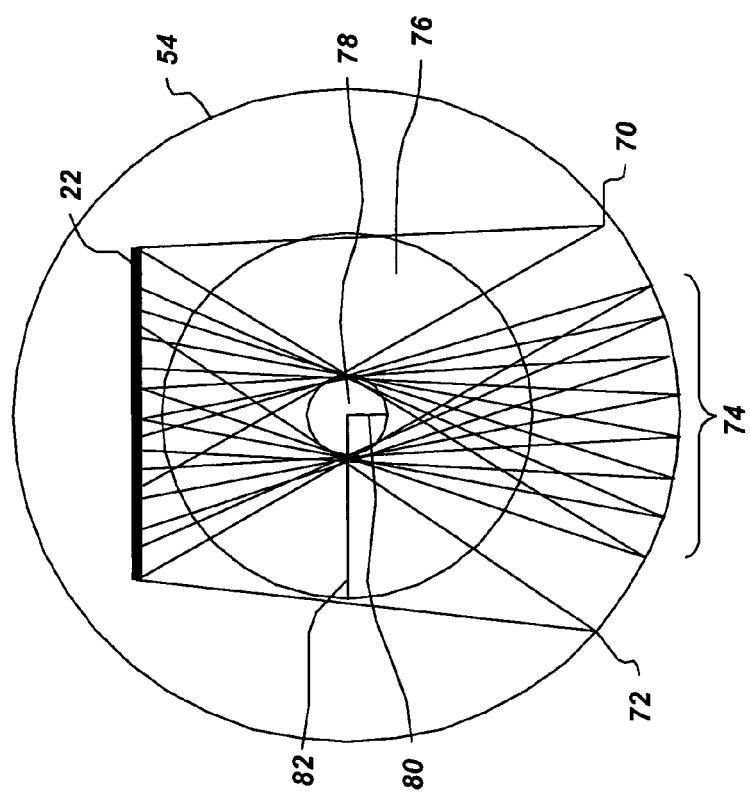
FIG. 3 is a diagrammatical illustration of a distributed source configuration for acquiring projection data in accordance with one aspect of the present technique.

FIG. 3 is a diagrammatical illustration of a distributed source configuration for acquiring projection data in accordance with one aspect of the present technique. As shown in FIG. 3, the gantry 54 includes two discrete emission points, indicated generally by the reference numerals 70 and 72 and an arc of discrete or continuous X-ray source points, indicated by the reference numeral 74. The arc of discrete or continuous X-ray source points 74 comprises a plurality of X-ray sources with spacing on the order of the view angle spacing. In an exemplary embodiment, seventy X-ray sources may be included in the arc of source points and the view angle spacing between the X-ray sources may be 0.3 degrees. The arc of X-ray source points 74 is configured to measure several samples of projection data at each view angle position. In one embodiment of the present technique, and as will be described in greater detail below, the discrete emission points 70 and 72 are configured to individually emit streams of radiation at multiple angular positions about a volume of interest, and the arc of discrete or continuous X-ray source points is configured to emanate X-ray beams illuminating a central region of interest 78. Further, the volume of interest (that is, the reconstructed image 64 shown in FIG. 2) may be comprised within the field of view 76.

Referring again to FIG. 3, the emission points 70 and 72 may include an X-ray tube, comprising an electron emitter utilizing field emission, thermionic emission, or any other means to produce the X-ray beam from a focal point when activated. The emission points may be rotated about the desired field of view 76, allowing each emission point to emit streams of radiation 16 from desired view angle positions. As the emission points 70 and 72 rotate, they may be alternatively activated such that only one emission point emits X-rays at a given time, or such that each detector cell is irradiated by no more than one emission point at any given time. Each emission point may be configured to emit a fan-shaped stream of radiation which when activated, illuminates a portion of the field of view 76. In accordance with a particular embodiment, the collimator 14 may be used to restrict the fan-beam to illuminate a portion of the field of view 76. The stream of radiation 16 passes through the field of view 76, and any attenuating matter within the field of view 76, before striking the detector 22, such as flat-panel detector. For each activation of an emission point, the data acquisition system 34 (FIG. 1) reads out the signals generated by the detector 22, which may be processed to generate the projection data. As the emission points rotate about the field of view 76 the combined or aggregate acquired projection data comprises the requisite projection data from the entire field of view 76. As mentioned previously, a stationary ring of X-ray source points may comprise the discrete emission points and the arc of discrete or continuous emission points, including a collimator to direct the X-ray beam to the appropriate regions of the field of view 76. For this embodiment, the requisite projection data is acquired by individual activation of the X-ray source points in such a manner to acquire the requisite projection data.

As will be appreciated by one of ordinary skill in the art, sufficient projection data to reconstruct the field of view 76 may be acquired with less than a full rotation (that is, 360°) of the emission points 70 and 72 about the field of view 76. As shown in FIG. 3, since the entire field of view 76 is not encompassed by the fan beam emitted by either of the discrete emission points 70 and 72, the in-plane size of the detector 22 is reduced. For example, the detector 22 may have a relatively small in-plane extent and, indeed, may be substantially flat, such as a flat panel detector. For example, for a radius 80 of the central region of interest 78 of 10 cm and a radius 82 of the field of view 76 of 25 cm, the detector 22 may be 30 percent or less of the size of a respective detector associated with the same field of view and a single emission point. The reduced in-plane extent of the detector 22 may allow smaller, less expensive detectors to be employed. For volumetric acquisitions, the smaller in-plane detector requirement implies that flat-panel detectors may be suitable for the acquisition.

Referring to FIG. 3, it may be observed that the X-ray emitted by the first emission point 70 and the second emission point 72 do not pass through the same regions of the field of view 76 as the arc of discrete or continuous X-ray source points 74. Because of this distinction between the discrete emission points 70 and 72 and the arc of discrete or continuous X-ray source points 74, the first and second emission points 70, 72 need not be operated equivalently, such as when the periphery of the field of view 76 is of less or no interest. For example, fewer views may be acquired using the discrete emission points 70 and 72 if desired. Additionally, the first and second emission points 70 and 72 may be operated for a reduced duration or duty cycle, or at a lower intensity relative to the arc of discrete or continuous X-ray source points 74.

Likewise, the discrete emission points 70 and 72 may be of lower performance characteristics i.e., lower flux, and so forth than the arc of discrete or continuous X-ray source points 74, if the peripheral region imaged by the discrete emission points 70 and 72 is less important. In particular, if lower attenuation, lower resolution, and/or higher noise are acceptable for the periphery of the region of interest, a lower flux may be required from discrete emission points 70 and 72. Differential activation of the first and second emission points 70, 72 and/or the use of a lower flux may allow different doses to be applied to the patient 18 at the center and periphery of the region of interest. In this manner, the dose received by the patient 18 may be customized based on the circumstances.

Though FIG. 3 depicts implementations including two emission points 70 and 72, the technique is extendable to more than two emission points or alternatively just a single emission point. For example, three or more X-ray tubes may be employed comprising solid-state or thermionic electron emission within the X-ray source, which includes three or more addressable discrete emission points configured in the path of the gantry 54. Other X-ray sources, which include discrete and addressable emission points, may also be suitable for use with the present techniques.

Referring to FIG. 4 now, a diagrammatical illustration of a distributed source configuration for acquiring projection data in accordance with another aspect, of the present technique is shown. As shown in FIG. 4, a portion of the field of view 76 is covered by a single emission point 70. Therefore, in this case, sufficient projection data to reconstruct the field of view 76 is acquired by a full rotation (that is, 360°) of the emission point 70 about the field of view 76. As mentioned previously, the rotational imaging scenario may be implemented with a ring of stationary, distributed X-ray source points.

Referring now to both FIGS. 3 and 4, in an exemplary operation of the present technique, the gantry 54 is rotated at a substantially slow rotation speed about the volume of interest to generate projection data, which are subsequently processed to generate one or more reconstructed images as will be described in greater detail below. As mentioned above, the path of the gantry includes one or more discrete emission points and an arc of discrete or continuous X-ray source points. In one aspect of the present technique, the discrete emission points 70 and 72 are configured to image the full field of view and the arc of discrete or continuous emission points 74 are configured to image a dynamic portion of the field of view. Further, in accordance with this aspect, the dynamic portion of the field of view comprises the central region of interest 78 of the patient 18, wherein the central region of interest comprises the heart. Further, in accordance with this aspect, the volume of interest includes the chest region of the patient 18, and the rotation time of the gantry is between about fifteen seconds and about twenty seconds to rotate the requisite angular range to acquire the necessary projection, the rotation time typically being equivalent to a single breath hold of the patient. Since the chest region may be assumed to be stationary outside the heart region, the slow rotation allows appropriate reconstruction in the volume of interest. It will be appreciated that the rotation speed can be varied according to the imaging application, field of view requirements, and the configuration of the discrete emission points with the arc of continuous or discrete emission points. To decrease the rotation time, the extent of the arc of source points must increase, as well as the extent of the detector and sampling rate of the data acquisition system. Hence the term "slow rotation speed" is meant to comprise system configurations where the rotation speed is slower than current state-of-the-art technology, but is appropriate given the clinically acceptable length of a patient's breath hold and the size and extent of the distributed X-ray source and detector.

Referring to FIG. 3 again, in an alternate implementation of the present technique, the discrete emission points 70 and 72 may also be configured to emit X-rays within a fan encompassing the central region of interest 78. Therefore, the discrete emission points may also be used to obtain projection data that encompasses the dynamic field of view that comprises the central region of interest 78.

FIG. 5 is a flowchart showing exemplary logic, including exemplary steps for generating projection data and processing the projection data to generate one or more reconstructed images, in accordance with one aspect of the present technique. Referring to FIG. 5, in step 86, a first projection data set is obtained, by individually activating the discrete emission points 70 and 72 at multiple angular positions about the volume of interest. As mentioned above, the volume of interest may be comprised within the field of view 76. The first projection data set comprises a plurality of projections. In particular, and as mentioned above, for each activation of an emission point, the data acquisition system 34 (FIG. 1) reads out the signals generated by the detector 22, which may be processed to generate the first projection data set.

In step 88, a second projection data set comprising a plurality of projections is obtained at a plurality of view angle positions, by activating the arc of discrete or continuous X-ray source points 74. As mentioned above, the arc of X-ray source points 74 is configured to emanate X-ray beams illuminating the central region of interest 78 and is used to image the central region of interest 78. In accordance with one embodiment of the present technique, the central region of interest comprises the heart undergoing a cardiac cycle.

In particular, a plurality of projections comprising the second projection data set is acquired at different instants in time with respect to the cardiac cycle at each view position. The streams of radiation 16 emanated from the arc of source points 74, passes through the central region of interest 78, and any attenuating matter within the central region of interest 78 before striking the detector 22, such as flat-panel detector. The data acquisition system 34 (FIG. 1) reads out the signals generated by the detector 22, which may be processed to generate the second projection data set.

It is to be appreciated that steps 86 and 88 need not be performed sequentially and may be performed substantially concurrently or in an interleaved manner.

In step 90, the plurality of projections comprising the second projection data set are interpolated to generate a set of time-resolved, interpolated projections. Each interpolated projection characterizes the projection data from the central region of interest 78 at a particular instant in time. As mentioned above, the central region of interest 78 includes a heart with a cardiac cycle.

In accordance with one embodiment of the present technique, interpolating the plurality of projections in step 90 comprises using a set of phase data and estimation of the frequency content information related to the plurality of projections. The frequency content of the projection data includes a priori information about characteristics of the motion in the heart as represented in the signals measured by corresponding elements of the detector 22. The phase data refers to the timing of the cardiac phases during the acquisition of the projection data and may be used to interpolate the projection data. The phase data may comprise an ECG signal acquired concurrently with the radiographs. Alternatively, phase data may comprise a pseudo-ECG signal derived from the projection data themselves such as via techniques employing consistency conditions to analyze the projection data and/or to compare the moments of the projection data.

Using the phase data and information about the frequency content in the projection data, the projections are correlated with the times that they correspond to in the cardiac cycle as well as with the angular positions of the gantry 54 to which they correspond. The projection data may then be interpolated, to generate interpolated projections. Because the two-dimensional projections appropriately capture the frequency content in the signal acquired at each detector element by design, the interpolated projections each correctly characterize the projection data at any instant in time with respect to the cardiac cycle at the respective view location. In this manner, projections acquired at discrete points in time may be converted into a continuous-time representation and, from the continuous time representation, the projections may be interpolated to a particular instant with respect to the cardiac cycle.

The conversion of discrete points into a continuous-time representation may be accomplished in a variety of ways known in the art. Likewise, the interpolation of values from a continuous-time representation using a suitable interpolation algorithm may be accomplished in various ways. For example, the Nyquist Theorem provides that, if a sufficiently high rate of discrete samples of a waveform are obtained, a continuous-time representation using the discrete-time samples may be generated. The Nyquist Theorem also provides that a sample value at a particular instant in time may be generated from the continuous-time representation of the signal. For example, a Fourier time series is a suitable continuous-time function for this purpose if the motion is periodic. Alternately, periodic splines or other continuous-time functions can be used for the decomposition.

In addition, the interpolation process provides a mechanism to reduce the statistical noise in the projection data. For example, a priori information about the frequency content of the relevant information pertaining to the cyclic motion of the heart in the projection data may be used to band-limit frequency components in the projection data. Band-limiting the frequency components may help reduce noise in the reconstructed images and may allow patient dose to be reduced while still achieving suitable quality of reconstructed images.

As noted above, the interpolated projections each correspond to a particular instant of the cardiac cycle at a respective view angle position. The interpolated projections corresponding to a desired instant of the cardiac cycle may therefore be reconstructed, to generate cardiac images at the desired instant of the cardiac cycle. In addition, because the interpolated projections are interpolated to the same instant in time, the reconstructed images and/or volumes have a high temporal resolution, typically less than 50 ms.

In step 92, the first projection data set and the set of interpolated projections are combined to generate one or more time-resolved reconstructed images. In accordance with the present technique, the reconstructed images include a reconstructed volume of interest and a reconstructed central region of interest. The combination of the first dataset and a time-resolved second dataset forms a complete time-resolved dataset, which is reconstructed using any existing reconstruction technique, resulting in a full-FOV time-resolved reconstructed image. The reconstructed images are substantially free of motion defects and artifacts, effectively "freezing" the cardiac motion at each point in time. The reconstructed images may, if desired be associated spatially and/or temporally to generate an image over time, a volume at an instant in time, or a volume over time.

The embodiments of the present technique described above, disclose a technique for performing a full field of view imaging of dynamic structures using a distributed source configuration in a CT system, with data acquisition and reconstruction principles that utilize interpolation-based reconstruction. The distributed source configuration disclosed in embodiments of the present technique, includes one or more discrete emitters and an arc of discrete or continuous source points to provide high spatial resolution and high temporal resolution imaging of dynamic structures by utilizing a two-dimensional detector with a reduced in-plane and/or axial extent.

The distributed source configuration disclosed by embodiments of the present technique, offers several advantages, including the ability to perform high spatial resolution imaging throughout the field of view, with reduced detector size and reduced patient dose. In addition, using the interpolation-based reconstruction technique described above, improved temporal resolution can be achieved for a central region of interest, using the arc of source points. As mentioned above, the interpolation-based reconstructions techniques can include methods to reduce noise in the projection data, thereby improving image quality or enabling dose reduction at the same image quality. Furthermore, the distributed source configuration reduces overall system complexity, since the gantry can be rotated slowly.

In addition, the present technique may also allow for the use of various detector technologies, such as energy discrimination detectors, so that CT techniques such as energy discrimination CT may be performed. Because of the smaller detector extent in the in-plane and/or longitudinal directions, such exotic technologies may more affordably be implemented. Similarly, such detectors may also be more easily manufactured to accommodate the reduced detector dimensions associated with the present techniques. In addition, the smaller fan angle associated with the present technique improves spatial resolution by minimizing the effective optical size of the focal spot within the image volume, reduces scatter in the X-ray intensity measurements and may allow the anti-scatter grid to be omitted from the detector, thereby increasing detector efficiency.

While the present techniques have been presented in the context of cardiac imaging, the techniques may be applied to the imaging of other dynamic objects. Discussion of cardiac imaging is presented merely to facilitate explanation of the present techniques. Indeed, while only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for Computed Tomography (CT) imaging, the method comprising:
    rotating a gantry at a substantially slow rotation speed about a volume of interest, wherein the gantry comprises a combination of X-ray source points, and wherein the X-ray source points comprise one or more discrete emission points and an arc of discrete or continuous X-ray source points;
    obtaining projection data from the combination of X-ray source points, comprising:
        obtaining a first projection data set by individually activating the one or more discrete emission points at multiple angular positions about the volume of interest; and
        obtaining a second projection data set at a plurality of view angle positions, by activating the arc of discrete or continuous X-ray source points to emanate X-ray beams illuminating a central region of interest; and
    performing a suitable reconstruction based on the projection data obtained from the combination of X-ray source points, and generating one or more reconstructed images.

2. The method of claim 1, wherein the rotation time of the gantry is between about fifteen seconds and about twenty seconds.

3. The method of claim 1, wherein the one or more discrete emission points comprise X-ray tubes.

4. The method of claim 1, wherein the one or more discrete emission points and the arc of discrete or continuous X-ray source points are rotated by mechanically rotating the emission points about the field of view.

5. The method of claim 1, wherein the one or more discrete emission points and the arc of discrete or continuous X-ray source points are individually activated in a sequential manner about a field of view.

6. The method of claim 1, further comprising interpolating a plurality of projections comprising the second projection data set to generate a set of time-resolved, interpolated projections, wherein each interpolated projection characterizes the projection data from the central region of interest at a particular instant in time.

7. The method of claim 6, wherein interpolating the plurality of projections comprising the second projection data set comprises using phase data related to the plurality of projections.

8. The method of claim 6, wherein interpolating the plurality of projections comprising the second projection data set comprises using a set of phase data and frequency content information related to the plurality of projections.

9. The method of claim 7, wherein the phase data is generated from the acquired projection data related to the plurality of projections.

10. A method for Computed Tomography (CT) imaging, the method comprising:
    rotating a gantry at a substantially slow rotation speed about a volume of interest, wherein the gantry comprises one or more discrete emission points and an arc of discrete or continuous X-ray source points;
    obtaining a first projection data set comprising a plurality of projections, by individually activating the one or more discrete emission points at multiple angular positions about the volume of interest;
    obtaining a second projection data set comprising a plurality of projections at a plurality of view angle positions, by activating the arc of discrete or continuous X-ray source points to emanate X-ray beams illuminating a central region of interest;
    interpolating the plurality of projections comprising the second projection data set to generate a set of time-resolved, interpolated projections, wherein each interpolated projection characterizes the projection data from the central region of interest at a particular instant in time; and combining the first projection data set and the set of interpolated projections and generating one or more time-resolved reconstructed images.

11. The method of claim 10, wherein the rotation time of the gantry is between about fifteen seconds and about twenty seconds.

12. The method of claim 10, wherein the one or more discrete emission points comprise X-ray tubes.

13. The method of claim 10, wherein the one or more discrete emission points and the arc of discrete or continuous X-ray source points are rotated by mechanically rotating the emission points about the field of view.

14. The method of claim 10, wherein the one or more discrete emission points and the arc of discrete or continuous X-ray source points are individually activated in a sequential manner about a field of view.

15. The method of claim 10, wherein interpolating the plurality of projections comprising the second projection data set comprises using a set of phase data and frequency content information related to the plurality of projections.

16. A Computed Tomography (CT) imaging system, the system comprising:

a gantry configured to rotate at a substantially slow rotation speed about a volume of interest, wherein the gantry comprises one or more discrete emission points and an arc of discrete or continuous X-ray source points, and wherein the one or more discrete emission points are configured to individually emit streams of radiation at multiple angular positions about the volume of interest and wherein the arc of discrete or continuous X-ray source points is configured to emanate streams of radiation illuminating a central region of interest;

a detector configured to detect the streams of radiation from the one or more discrete emission points and the arc of discrete or continuous X-ray source points, and generate one or more signals responsive to the streams of radiation; and a computer configured to receive and process the one or more signals from the detector to generate projection data and perform a suitable reconstruction on the projection data, and generating one or more reconstructed images, wherein the computer is further configured to obtain;

a first projection data set, wherein the first projection data set is generated by individually activating the one or more discrete emission points at multiple angular positions about the volume of interest; and a second projection data set, wherein the second projection data set is generated at a plurality of view angle positions, by activating the arc of discrete or continuous X-ray source points to emanate X-ray beams illuminating a central region of interest.

17. The system of claim 16, wherein the rotation time of the gantry is between about fifteen seconds and about twenty seconds.

18. The system of claim 16, wherein the one or more discrete emission points comprise X-ray tubes.

19. The system of claim 16, wherein the one or more discrete emission points and the arc of discrete or continuous X-ray source points are rotated by mechanically rotating the emission points about the field of view.

20. The system of claim 16, wherein the one or more discrete emission points and the arc of discrete or continuous X-ray source points are individually activated in a sequential manner about a field of view.

21. The system of claim 16, wherein the computer is further configured to interpolate a plurality of projections comprising the second projection data set using a set of phase data and frequency content information related to the plurality of projections.

* * * * *